(12) United States Patent
Zanda et al.

(10) Patent No.: US 7,999,101 B2
(45) Date of Patent: Aug. 16, 2011

(54) CATIONIC LIPIDS FOR THE TRANSFECTION OF NUCLEIC ACIDS

(75) Inventors: Matteo Zanda, Bergamo (IT); Luca Bruche', Milan (IT); Massimo Frigerio, Verona (IT); Fiorenza Viani, Milan (IT); Luca Chiamenti, Varese (IT); Walter Panzeri, Milan (IT); Nadia Zaffaroni, Milan (IT); Marco Folini, Milan (IT); Maria Angela Greco, Milan (IT)

(73) Assignee: Politecnico Di Milano, Milan (IT)

( * ) Notice: Subject to any disclaimer, the term of this patent is extended or adjusted under 35 U.S.C. 154(b) by 0 days.

(21) Appl. No.: 11/884,354

(22) PCT Filed: Feb. 13, 2006

(86) PCT No.: PCT/IT2006/000072
§ 371 (c)(1),
(2), (4) Date: Aug. 15, 2007

(87) PCT Pub. No.: WO2006/087752
PCT Pub. Date: Aug. 24, 2006

(65) Prior Publication Data
US 2008/0146518 A1 Jun. 19, 2008

(30) Foreign Application Priority Data
Feb. 15, 2005 (IT) .............. MI2005A0222

(51) Int. Cl.
*C07D 251/54* (2006.01)
*C07D 251/70* (2006.01)
*A61K 31/53* (2006.01)
*A61K 31/7105* (2006.01)
*A61K 31/711* (2006.01)
*A61P 43/00* (2006.01)
*C12N 15/00* (2006.01)

(52) U.S. Cl. ....... 544/196; 544/197; 544/198; 536/22.1; 536/23.1; 435/366; 435/375; 977/773; 977/788; 977/792; 977/906; 977/915

(58) Field of Classification Search .................. 544/196, 544/197, 198; 514/245
See application file for complete search history.

(56) References Cited

U.S. PATENT DOCUMENTS

| 3,755,322 | A | * | 8/1973 | Winter et al. | 544/197 |
| 5,736,392 | A | | 4/1998 | Hawley-Nelson et al. | |
| 2004/0077648 | A1 | * | 4/2004 | Timmer et al. | 514/241 |

FOREIGN PATENT DOCUMENTS

| DE | 2038182 | 2/1972 |
| SU | 657 048 A1 | 4/1979 |
| WO | WO 99/51581 | 10/1999 |

OTHER PUBLICATIONS

J.N. Ashley et al., "The Search for Chemotherapeutic Amidines. Part XVI. Amidinoanilino-1,3,5-triazines and Related Compounds." Journal of the Chemical Society, Chemical Society, Letchworth, GB, 1960, pp. 4525-4532, XP000573907.
Piotr Lipkowski et al., "Self-assembly of a [2×2] hydrogen bonded grid," Chemical Communications—Chemcom, Royal Society of Chemistry, GB, 1999, pp. 1311-1312, XP-002165632.
Takeshi Kajiki et al., "Functionalized Flavin Receptors. Regulation of Redox Properties of 6-Azaflavin via Hydrogen Bondings with Melamine Derivatives Bearing Guanidinium Ion(s) in Organic Solvents," J. Org. Chem. 1999, vol. 64, pp. 9679-9689, XP-002378892.
Maria Arduini et al., "A Novel Type of Hydrogen-Bonded Assemblies Based on the Melamine-Cyanuric Acid Motif," Journal of Organic Chemistry, 68(3), pp. 1097-1106 Coden: Joceah, ISSN: 0022-3263, 2003, XP-002378893.
Rongxiu Li et al., "Design, synthesis, and application of a Protein A mimetic," Nature Biotechnology, vol. 16, No. 2, pp. 190-195, Feb. 1998, Coden: NABIF9, ISSN: 1087-0156, XP002966694.
H. Graubaum et al., "Polyazacalix[5]arene—Synthese und NMR-Untersuchungen," vol. 339, No. 3, 1997, pp. 266-271, XP009065733.
Emmanuel Dauty et al., "Dimerizable Cationic Detergents with a Low cmc Condense Plasmid DNA into Nanometric Particles and Transfect Cells in Culture," Journal of the American Chemical Society, vol. 123, No. 38, Sep. 26, 2001, pp. 9227-9234, XP002378894.

* cited by examiner

*Primary Examiner* — Venkataraman Balasubramanian
(74) *Attorney, Agent, or Firm* — Arent Fox LLP

(57) ABSTRACT

The present invention relates to cationic lipids capable of forming complexes with nucleic acids and the use thereof for the transfection of eukaryotic cells. The cationic lipids according to the invention have general formulas (I) and (Ia):

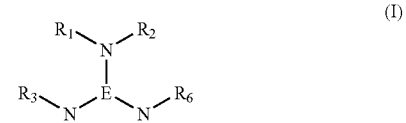

(I)

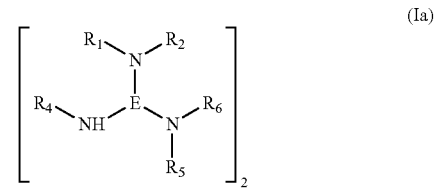

(Ia)

Figure 1:
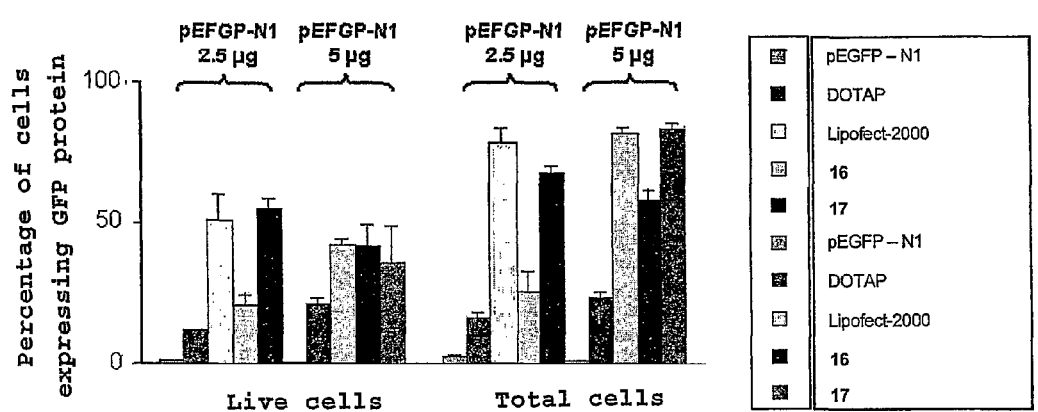

(see formulas (I) and (Ia), wherein E is a heteroaryl; R1 and R2 are selected from H, —R7—NH$_2$, alkyl; R7 is selected from alkyl, alkenyl, aryl, (C$_1$-C$_{20}$) alkyl-aryl-(C$_0$-C$_{20}$) alkyl; R3 and R4 are selected from: H, —R8—SH, R8—NH—NH$_2$/—R8—CO—R9 or —R8—NH$_2$; R8 is selected from: alkyl, alkenyl, aryl, (C$_1$-C$_{20}$) alkyl-aryl-(C$_0$-C$_{20}$) alkyl; R9 is selected from: H, alkyl; R5 and R6 are selected from: H, alkyl, alkenyl, aryl, (C$_1$-C$_{20}$) alkyl-aryl.

38 Claims, 1 Drawing Sheet

CATIONIC LIPIDS FOR THE TRANSFECTION OF NUCLEIC ACIDS

CROSS-REFERENCE TO RELATED APPLICATION

This application is a National Stage entry of International Application No. PCT/IT2006/000072, filed Feb. 13, 2006, the entire specification claims and drawings of which are incorporated herewith by reference.

The present invention relates to cationic lipids capable of forming complexes with nucleic acids and the use thereof for the transfection of eukaryotic cells.

Transfection consists in the transfer of exogenous DNA molecules into target cells. Once transfected, the DNA will be maintained in the cytoplasm by many cells for a determined period of time, generally 2-3 days (transient transfection) while in only a few cases will it be integrated into the cellular genome (stable transfection) [for a review of this topic, please see for example: *J. Gene Med.* 2004, 6, S24-S35; *Angew. Chem. Int. Ed.* 2003, 42, 1448]. The technique may also be applied to RNA.

As is now known, cells are not capable of naturally taking-up DNA, in that during the course of evolution, mechanisms have been developed for impeding the entry of exogenous DNA (physical barriers such as the cell membrane, intracellular defence systems represented by enzyme cascades, ready to eradicate foreign material etc.). Hence, in order to bypass the natural barriers against gene transfer, various methods based on "chemical" (such as liposomes and cationic lipids), physical (such as electroporation and microinjection), and "biological" vectors (such as viruses) have been developed.

The use of chemical reagents for transfection has been introduced in 1965 with the discovery of DEAE-Dextran, a cationic polymer which binds tightly to the negatively charged phosphate groups of DNA. These large DNA-containing particles adhere to the surface of cells and are internalised by means of endocytosis. Though technically simple, this method is not very efficient for many cell types, and hence not very reliable for routine biological activity assays of purified DNA preparations.

Cationic lipids, which are amphiphilic molecules by nature, are particularly interesting. The cationic head of the lipid compound associates tightly with the negatively charged phosphate groups on the nucleic acids. The lipid/DNA-RNA complexes combine and then fuse with cellular membranes, and are thus internalised into the cell. This method is very advantageous for numerous reasons: for example, because the DNA is released efficiently into various cell types.

Some groups have reported the use of cationic lipids functionalised with a thiol function, which, following complexing with the DNA or RNA molecules give rise to the formation of disulphide bridges even under mildly oxidising conditions (for example simply in the presence of atmospheric oxygen), thus stabilising the DNA (or RNA) nanoparticles [see for example: Behr et al. *J. Am. Chem. Soc.* 2001, 123, 9227]. Once the nanoparticles are internalised, the reducing intracellular environment results in the cleavage of the disulphide bonds with the consequent liberation of the genetic material. Furthermore, it seems that the disulphide bonds contribute towards the permeation of the cellular membrane, facilitating the internalisation of the DNA/RNA.

However, there is still a need to continue the search for novel molecules with good genetic material complexing and internalising capacity, additionally characterised by low cytotoxicity.

The present invention is hereinafter described referring also to the annexed FIGURE, wherein:

FIG. 1 is a graph showing the percentage of GFP expression in PC3 cells as a function of various transfection agents.

Hence, in a first aspect, the invention concerns amphiphilic compounds and pharmaceutically acceptable salts thereof, of formula (I):

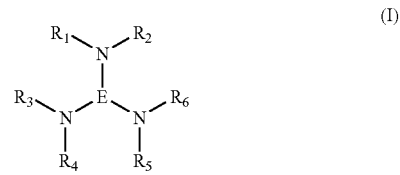

wherein E is a heteroaryl selected from: triazine, pyrimidine, pyridine, pyrazine, pyridazine, pyrrole, pyrazole, imidazole, furan, thiazole, isothiazole, oxazole, isoxazole, thiophene, quinoline, quinolizine, purine, isoquinoline, indole, indazole, isoindole, benzofuran, isobenzofuran, phenazine, carbazole, xanthene, phthalazine, quinoxaline, pteridine, purine, acridine, phenanthroline, phenanthridine;

R1 and R2, being identical or different, but never simultaneously equal to H, are selected from: H, —R7-$NH_2$, —CH—NH—$NH_2$, linear or branched alkyl with from 1 to 10 carbon atoms or, together with the nitrogen atom to which they are bound, may form a 5 or 6 member heterocyclic ring; R7 is selected from: a linear or branched alkyl with from 2 to 10 carbon atoms, a linear or branched alkenyl, with from 3 to 10 carbon atoms and from 1 to 5 double bonds, an aryl or ($C_1$-$C_{20}$)alkyl-aryl-($C_0$-$C_{20}$)alkyl;

R3 and R4, being identical or different, but never simultaneously equal to H, are selected from: H, —R8-SH, —R8-NH—$NH_2$, —R8-CO—R9 or —R8-$NH_2$;

R8 is selected from: a linear or branched alkyl with from 2 to 10 carbon atoms, a linear or branched alkenyl, with from 3 to 10 carbon atoms and from 1 to 5 double bonds, an aryl or ($C_1$-$C_{20}$) alkyl-aryl-($C_0$-$C_{20}$)alkyl;

R9 is selected from: H or linear or branched alkyl with from 1 to 10 carbon atoms;

R5 and R6, being identical or different, but never simultaneously equal to H, are selected from: H, linear or branched alkyl with from 6 to 20 carbon atoms, a linear or branched alkenyl with from 6 to 20 carbon atoms and with from 1 to 10 double bonds, aryl or ($C_1$-$C_{20}$)alkyl-aryl;

Preferably, E is selected from: triazine, pyrimidine, pyridine, pyrazine, pyridazine, pyrrole, pyrazole, imidazole, furan, thiazole, isothiazole, oxazole, indole, isoquinoline, phthalazine.

More preferably, E is selected from: triazine, pyrimidine, pyridine, pyrazine, pyridazine, pyrrole, pyrazole, imidazole, phthalazine.

Even more preferably, E is selected from: triazine or pyrimidine.

Preferably, R1 and R2 are selected from: H, —R7-$NH_2$, linear alkyl with from 1 to 6 carbon atoms or, together with the nitrogen atom to which they are bound, form a heterocycle selected from: 1,4-diazacyclohexane, 1,3-diazacyclohexane, 1,2-diazacyclohexane, piperidine, pyrrolidine, morpholine. More preferably, R1 and R2 are selected from: H, methyl, ethyl, propyl, n-butyl, n-pentyl, —R7-$NH_2$ or form 1,4-diazacyclohexane, 1,3-diazacyclohexane or 1,2-diazacyclohexane. Even more preferably, R1 and R2 are H, —R7-$NH_2$, methyl or form 1,4-diazacyclohexane.

Preferably R7 is a linear alkyl with from 2 to 6 carbon atoms, benzyl, ($C_1$-$C_5$) alkyl-aryl-($C_0$-$C_6$)alkyl. More preferably, R7 is an ethyl, propyl, n-butyl, n-pentyl, benzyl, phenyl, ($C_1$-$C_5$)alkyl-aryl-($C_0$-$C_3$) alkyl. Even more preferably R7 is propyl, benzyl or phenyl.

Preferably, R3 and R4 are selected from: H, —R8-SH, —R8-$NH_2$. More preferably, R3 and R4 are H or —R8-SH.

Preferably, R8 is a linear alkyl with from 2 to 6 carbon atoms, benzyl, ($C_1$-$C_5$)alkyl-aryl-($C_0$-$C_6$)alkyl. More preferably, R8 is an ethyl, propyl, n-butyl, n-pentyl, benzyl, phenyl, ($C_1$-$C_5$) alkyl-aryl-($C_0$-$C_3$) alkyl. Even more preferably R8 is ethyl, benzyl or phenyl.

Preferably, R9 is a linear alkyl with from 1 to 4 carbon atoms or H. More preferably, R9 is methyl, ethyl, propyl. Even more preferably, R9 is a methyl or H.

Preferably, R5 and R6 are selected from: H, linear alkyl with from 6 to 14 carbon atoms, ($C_1$-$C_4$)alkyl-aryl, benzyl. More preferably, R5 and R6 are H, n-hexyl, n-tetradecanoyl, phenyl.

The compound of formula (I) may, optionally, couple with one or more amphiphilic molecules to give a dimer of formula (Ia):

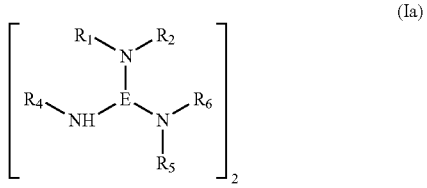

wherein R1, R2, R4, R5 and R6 are as described above.

Dimerisation may occur following complexing of the compounds of formula (I) with the nucleic acids, at physiological pH and in a mildly oxidising environment, for example in the presence of atmospheric oxygen.

In this case, the groups responsible for the dimerisation are the —SH, —NH—$NH_2$, —CO— and —$NH_2$ functionalities of R4, which react with the —SH, —CHO, —$NH_2$ and —CO— functionalities, respectively, of another molecule of formula (I).

The reaction between the two —SH groups leads to the formation of an —S—S— disulphide bond; the reaction between —NH—$NH_2$ and —CHO gives rise to a hydrazone —NHN=CH— and the reaction between —$NH_2$ and —CO— gives rise to an enamine —NH—C=C—. Once the complex between the dimer (Ia) and the nucleic acids penetrates into the cell, the reducing interior environment results in the cleavage of the disulphide, hydrazone or enamine with the consequent destabilisation of the complex, and release of the genetic material.

Alternatively, the compounds of formula (Ia) may be synthesised, as described in the following scheme 1, and then complexed with the nucleic acids.

The preferred compounds of the invention are:

2-[4-(3-amino-propylamino)-6-tetradecylamino-[1,3,5]triazin-2-ylamino]-ethanethiol;

the disulphide dimer of 2-[4-(3-amino-propylamino)-6-tetradecylamino-[1,3,5]triazin-2-ylamino]-ethanethiol;

2-[4-(2-N-piperazinyl)-6-tetradecylamino-[1,3,5]triazin-2-ylamino]-ethanethiol;

the disulphide dimer of 2-[4-(2-N-piperazinyl)-6-tetradecylamino-[1,3,5]triazin-2-ylamino]-ethanethiol;

2-[4-(2-amino-propylamino)-6-benzylamino-[1,3,5]triazin-2-ylamino]-ethanethiol;

2-[4-(2-amino-propylamino)-6-hexylamino-[1,3,5]triazin-2-ylamino]-ethanethiol;

N-(3-amino-propyl)-N'',N''-dimethyl-N'-tetradecyl-benzene-1,3,5-triamine.

Since at physiological pH the amino groups of the compounds of formulas (I) and (Ia) are protonated, they are capable of condensing negatively charged nucleic acids, forming complexes. Said complexes are also known as nucleic acid nanoparticles.

Such nanoparticles are capable of penetrating inside cells and releasing the genetic material (transfection), as previously explained in detail.

However, in a second aspect, the present invention also relates to nanoparticles for the in vivo and in vitro transfection of eukaryotic cells with nucleic acids, comprising one or more nucleic acids condensed with one or more compounds of formula (I) or (Ia).

Said nucleic acids are DNA and/or RNA. Preferably, the DNA is a plasmid encoding a therapeutically active molecule, for example a protein.

In vitro, the eukaryotic cells transfected with the nanoparticles of the invention are generally microorganisms, for example *E. coli*. Once transfected, said microorganisms are cultivated using techniques known in the art, for the production of molecules of biological interest (for example proteins).

The nanoparticles of the invention are used in vivo for the preparation of a medication for gene therapy, and administered locally (e.g. intramuscularly or subcutaneously) and systemically to mammals. For this purpose, pharmaceutical formulations comprising a therapeutically effective quantity of nanoparticles may also be prepared.

The present invention also provides a kit for the preparation of nanoparticles, comprising previously prepared, premeasured and prepacked raw materials, as well as the relevant disposable materials, for in vitro and in vivo transfections.

The kit will hence comprise appropriate genetic material, the compounds of formulas (I) and/or (Ia), appropriate buffers and other reagents and/or materials useful for preparing, purifying and applying the nanoparticles in vitro and in vivo.

Nanoparticles for the transfection of eukaryotic cells are prepared by mixing the nucleic acids with compounds of formula (I) in an appropriate buffer at physiological pH, for the amount of time necessary for the formation of the complex: compounds of formula (I)/nucleic acids. If the environment is mildly oxidising, for example in the presence of atmospheric oxygen, then following the complexing of the nucleic acids, the compounds of formula (I) may become dimerised. Alternatively, compounds of formula (Ia) may be used, already in dimeric form. As already explained previously, once the nanoparticles are internalised, the reducing intracellular environment leads to the cleavage of the dimer, with consequent destabilisation of the complex and release of the genetic material.

The compounds of formulas (I) and (Ia) have been prepared starting from commercially available reagents, by following the synthetic procedures illustrated in the following scheme 1. In any case, they may also be synthesised in any other manner, for example by using solid phase synthetic techniques, without departing from the scope of the invention.

Scheme 1

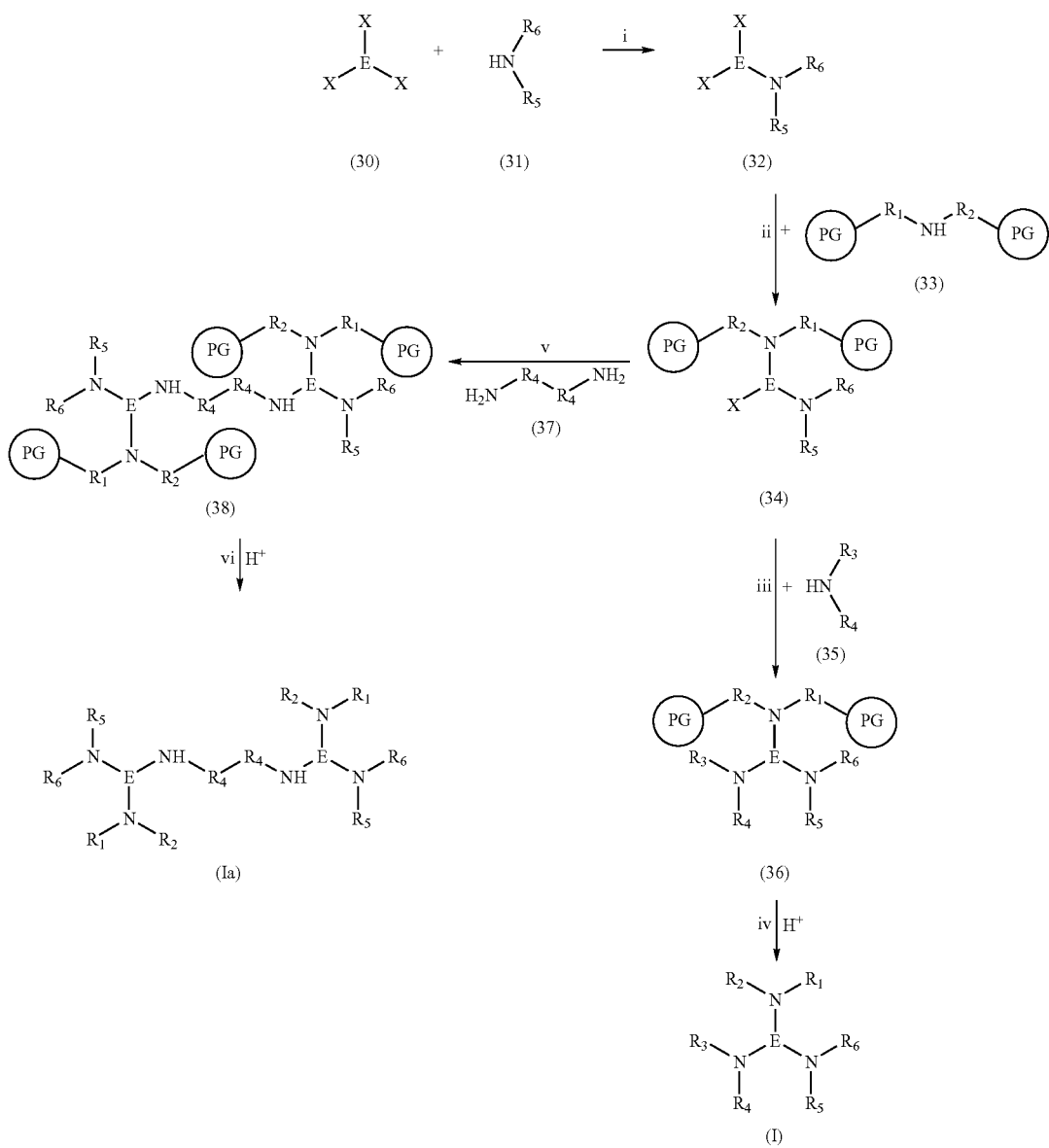

As shown in scheme 1, the compounds of formula (I) are synthesised starting from commercially available starting materials, (30) and (31), by means of three consecutive aromatic nucleophilic substitution reactions, (i), (ii) and (iii), and a final step, (iv), involving acid treatment.

Particularly, to a suspension of (30) in an appropriate mixture of solvents, for example water and acetone, THF (tetrahydrofuran), benzene, dioxan, toluene, acetonitrile, preferably water and acetone, THF or benzene, at a temperature of between 0° C. and 10° C., preferably around 0° C., is added dropwise a solution of amine (31) in an appropriate organic solvent, for example acetone, THF (tetrahydrofuran), benzene, dioxan, toluene, acetonitrile, preferably acetone, THF or benzene.

An aqueous solution of an inorganic base, for example $NaHCO_3$, NaOH, $Na_2CO_3$ preferably $NaHCO_3$, is then added dropwise. The mixture obtained is left stirring for from 1 to 24 hours, preferably from 2 to 12 hours, preferably at room temperature.

The reaction intermediate (32) is then purified by means of any technique known in the art, for example, by extraction in organic solvent and subsequent purification using a chromatography column.

Following purification, the intermediate (32) is suspended in a mixture of solvents, for example water and acetone, THF (tetrahydrofuran), benzene, dioxan, toluene, acetonitrile, preferably water and acetone, THF or benzene, at a temperature of between 0° C. and 10° C., preferably around 0° C. To this suspension of (32) is then added dropwise a solution of (33) in an appropriate organic solvent, for example acetone, THF (tetrahydrofuran), benzene, dioxan, toluene, acetonitrile, preferably acetone, THF or benzene.

An aqueous solution of an inorganic base, for example $NaHCO_3$, NaOH, $Na_2CO_3$, preferably $NaHCO_3$, is then added dropwise. The mixture obtained is left stirring for from 1 to 24 hours, preferably from 2 to 12 hours, at a temperature of from 25° C. to 70° C., preferably around 50° C.

The reaction intermediate (34) is then purified by means of any technique known in the art, for example, by extraction in organic solvent and subsequent purification using a chromatography column.

In scheme 1, the symbol "PG" means "protective group". When R1 and R2 are —R7-NH$_2$, —CH—NH—NH$_2$ or, together with the nitrogen to which they are bound, form a heterocyclic 6 member ring containing a second nitrogen atom, the primary amine, the guanidine and one of the secondary amines of the heterocyclic ring, must be protected prior to the aromatic nucleophilic substitution of step (ii). The protective groups used in the present invention are those known in the sector for the protection of amines and guanidines. For example, they are selected from: a tert-butoxycarbonyl (Boc), carbobenzyloxy (Cbz) group.

Following purification, the intermediate (34) is dissolved in an appropriate organic solvent, for example benzene, THF (tetrahydrofuran), dioxan, toluene, acetonitrile, preferably benzene or THF. To this solution is added the compound (35) together with a base, such as DIPEA (diisopropylethylamine), triethylamine, pyridine, preferably DIPEA. Preferably, the hydrochloride, hydrobromide or hydroiodide of the compound (35) is used for this reaction. More preferably, the hydrochloride of (35).

The mixture obtained is then stirred at a temperature of between 50° C. and 150° C., preferably at around 120° C., for the amount of time necessary for the reaction to go to completion. Preferably, this reaction is carried out in a hermetically sealed vial placed in an oscillating shaker.

The trisubstitution derivative (36) is then purified by means of any technique known in the art, for example, by extraction in organic solvent and subsequent purification using a chromatography column.

The intermediate (36) is dissolved in an organic solvent, preferably dichloromethane, and a solution of an organic acid, in the same solvent, added. The acid solution used is preferably 20% trifluoroacetic acid in dichloromethane. The mixture is kept stirring for 0.5-3 hours, preferably for approx. 1 hour. The solvent is then evaporated and the product (I) isolated as the salt of the acid.

Alternatively, the dimer (Ia) may be obtained by making the intermediate (34) react with the compound (37), wherein R4 is —R8-SH, —R8-NH—NH$_2$, —R8-CO—R9 or —R8-NH$_2$, and R8 and R9 are as described above. The reaction is carried out in an organic solvent, preferably acetone, with an excess of (34) with respect to (37), preferably using the hydrochloride, hydrobromide or hydroiodide of (34).

Afterwards, the intermediate (38) is purified using techniques known in the art, preferably by column chromatography, and then subjected to acid treatment, as described above for step (iv). The dimer (Ia) is isolated as the salt of the acid.

Some examples of preparation of the compounds of the invention are described hereinafter, by way of non-limiting representation.

EXPERIMENTAL SECTION

TLC is performed using Merck silica gel 60 F$_{254}$; flash chromatography has been performed using columns of silica gel 60 (60-200 μm, Merck). The $^1$H, $^{13}$C and $^{19}$F spectra have been recorded on Bruker ARX 400 or Bruker Ac 250 L spectrometers operating at 400 and 250 MHz, respectively. Chemical shifts are expressed in ppm (δ), using tetramethylsilane (TMS) as internal standard for the $^1$H and $^{13}$C nuclei ($δ_H$=0.00), while C$_6$F$_6$ has been used as the internal standard for $^{19}$F ($δ_F$=162.90). The mass spectra have been recorded on a TSQ quadruple mass spectrometer. Infrared spectra have been acquired using a Perkin Elmer System 2000 FT-IR (scanning field: 15600 cm$^{-1}$; combined scanning directions).

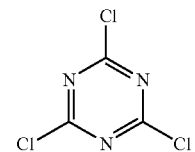

(1)

First aromatic nucleophilic substitution. General procedure. A solution of amine (1.0 mmol) in acetone is added dropwise to a suspension of 2,4,6-trichloro-[1,3,5]triazine (1) (1 mmol, 184 mg) in acetone (4 ml) in cold water (0° C.-1 ml). Afterwards, a solution of NaHCO$_3$ (1 mmol, 84 mg) in water (2 ml) is added dropwise, and the reaction left stirring for a time varying between two to twelve hours at room temperature. The progress of the reaction is monitored by TLC (n-hexane/ethyl acetate from 9:1 to 7:3), the acetone removed under reduced pressure, water (1 ml) added, and the organic phase extracted with ethyl acetate (3×1 ml) and with chloroform (2×5 ml). The combined extracts are dried over sodium sulphate, filtered, and the solvents removed under reduced pressure and the crude compound purified by flash chromatography in n-hexane/ethyl acetate, to give the first intermediate.

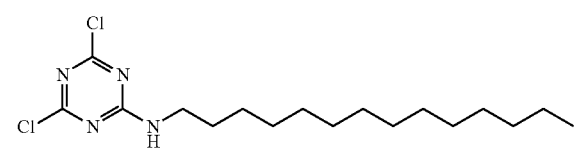

(2)

(a) Synthesis of (4,6-dichloro-[1,3,5]triazin-2-yl)-tetradecyl-amine (2).

Using 1-tetradecylamine (213 mg) as reagent, the reaction is given a time of two hours and the progress of the reaction monitored using n-hexane/ethyl acetate 9:1. The crude product is purified in the same solvent mixture and (2) is obtained with a yield of 67% (85% conversion); R$_F$=0.35.

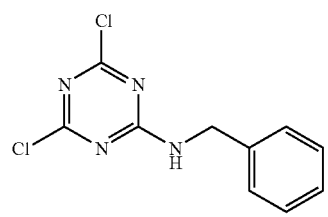

(3)

(b) Synthesis of (4,6-dichloro-[1,3,5]triazin-2-yl)-benzyl-amine (3). Using benzylamine (107 mg) as reagent, the reaction is given a time of ten hours and the progress of the reaction monitored using n-hexane/ethyl acetate 8:2. The crude product is purified in the same solvent mixture and (3) is obtained with a yield of 78%.

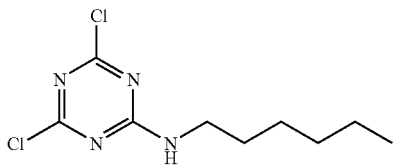
(4)

(c) Synthesis of (4,6-dichloro-[1,3,5]triazin-2-yl)-hexylamine (4). Using n-hexylamine (101 mg) as reagent, the reaction is given a time of twelve hours and the progress of the same monitored using n-hexane/ethyl acetate 9:1. The crude product is purified in the same solvent mixture and (4) is obtained with a yield of 86%.

Second aromatic nucleophilic substitution. General procedure. A solution of N-Boc monoprotected diamine (0.4 mmol) in acetone is added dropwise to a suspension of (2)-(4) (0.4 mmol) in water (0° C.-4 ml) and acetone (1.5 ml). A solution of NaHCO₃ (0.4 mmol, 34 mg) in water (2.5 ml) is added dropwise and the reaction left stirring using a magnetic stirrer for a period of time varying between two and twelve hours at 50° C. The progress of the reaction is monitored by TLC (n-hexane/ethyl acetate), the acetone is removed under reduced pressure, water (1 ml) is added and the organic phases extracted with ethyl acetate (3×5 ml) and chloroform (2×2.5 ml). The combined extracts are dried over sodium sulphate, filtered and the solvents evaporated under reduced pressure and the crude reaction product purified by means of flash chromatography.

(5)

(a) Synthesis of the tert-butyl ester of [3-(4-chloro-6-tetradecylamino-[1,3,5]triazin-2-ylamino)-propyl]carbamic acid (5). Starting from a solution of the (3-amino-propyl)-tert-butyl ester of carbamic acid (70 mg) the reaction mixture is left stirring using a magnetic stirrer for two hours, monitoring the progress of the same by n-hexane/ethyl acetate 7:3. The crude product is purified in n-hexane/ethyl acetate 7:3 and pure ethyl acetate for the final fractions to give (5) with a yield of 97%: $R_F$=0.35.

(6)

(b) Synthesis of the tert-butyl ester of [3-(4-chloro-6-tetradecylamino-[1,3,5]triazin-2-yl-piperazinyl)]carbamic acid (6). Starting from a solution of tert-butyl piperazine-1-carboxylate (74 mg) the reaction mixture is left stirring using a magnetic stirrer for two hours, monitoring the progress of the same by n-hexane/ethyl acetate 7:3. The residue is purified in n-hexane/ethyl acetate 7:3 and pure ethyl acetate for the final fractions to give (6) with a yield of 45%; $R_F$=0.35.

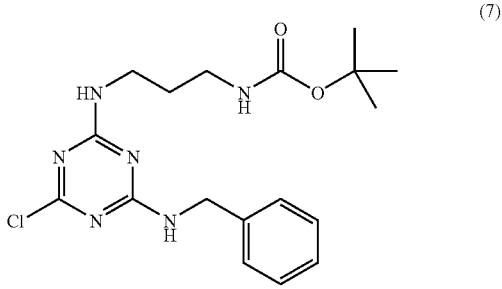
(7)

(c) Synthesis of the tert-butyl ester of [3-(4-chloro-6-benzylamino-[1,3,5]triazin-2-ylamino)-propyl]carbamic acid (7). Starting from a solution of the (3-amino-propyl)-tert-butyl ester of carbamic acid (70 mg) the reaction mixture is left stirring using a magnetic stirrer for twenty four hours, monitoring the progress of the same by n-hexane/ethyl acetate 8:2. The crude product is purified in n-hexane/ethyl acetate 7:3 to give (7) with a yield of 96%; $R_F$=0.35.

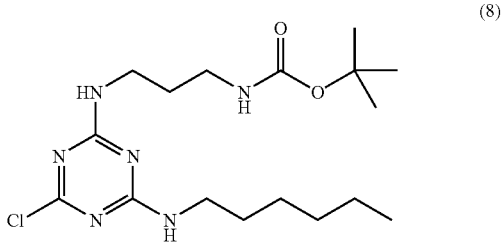
(8)

(d) Synthesis of the tert-butyl ester of [3-(4-chloro-6-hexylamino-[1,3,5]triazin-2-ylamino)-propyl]carbamic acid (8). Starting from a solution of the (3-amino-propyl)-tert-butyl ester of carbamic acid (70 mg) the reaction mixture is left stirring using a magnetic stirrer for twenty four hours, monitoring the progress of the same by n-hexane/ethyl acetate 7:3. The crude product is purified using the same eluent mixture to give 8 with a yield of 90%; $R_F$=0.35.

Third nucleophilic substitution General procedure. A solution of the 6-chloro-2,4-diamino-triazine derivative (0.40 mmol) in benzene (3 ml) is placed in a vial. The amine hydrochloride (0.80 mmol) and the DIPEA (2.0 mmol, 258 µl) are added at room temperature. The vial is hermetically sealed and placed in an oscillating shaker at 120° C. After checking by TLC (n-hexane/ethyl acetate), the mixture is evaporated under reduced pressure until a residue is obtained which, following purification by flash chromatography allows the isolation of the trisubstituted derivative.

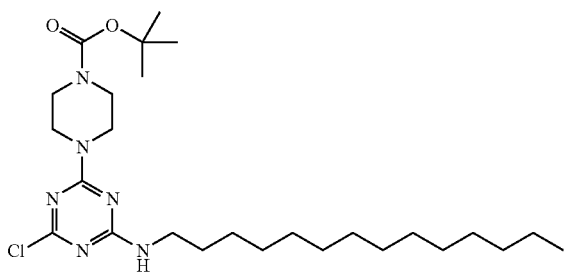

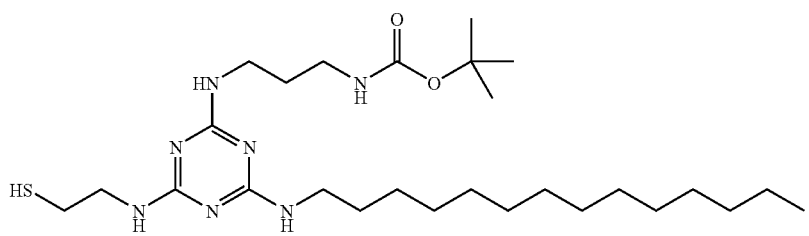

(9)

(a) Synthesis of the tert-butyl ester of {3-[4-(2-mercapto-ethylamine)-6-tetradecylamino-[1,3,5]triazin-2-ylamino]-propyl}carbamic acid (9).

From a solution of (5) (200 mg) and 2-amino-ethanethiol hydrochloride (180 mg) mixing for 24 hours, monitoring the progress in n-hexane/ethyl acetate 1:1 and chromatographing in ethyl acetate/methanol 7:3, is isolated (9) with a yield of 65%; $R_F$=0.35.

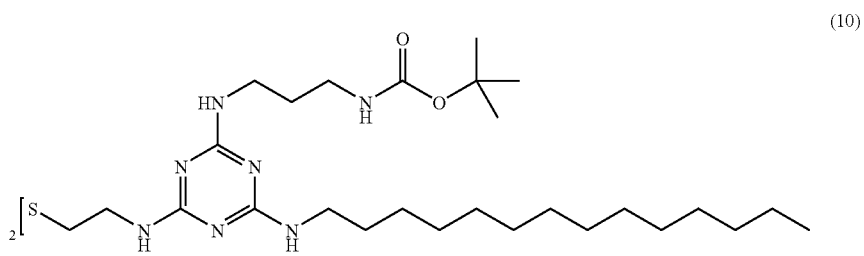

(10)

(b) Synthesis of the disulphide 10. From a solution of (5) (200 mg) and 2-(2-amino-ethyldisulphanyl)-ethylamine hydrochloride (90 mg) or the corresponding hydroiodide (163 mg) mixing for 24 hours, monitoring the progress in n-hexane/ethyl acetate 1:1 and chromatographing in ethyl acetate/methanol 7:3, is isolated the dimer (10) with a yield of 10%; $R_F$=0.35.

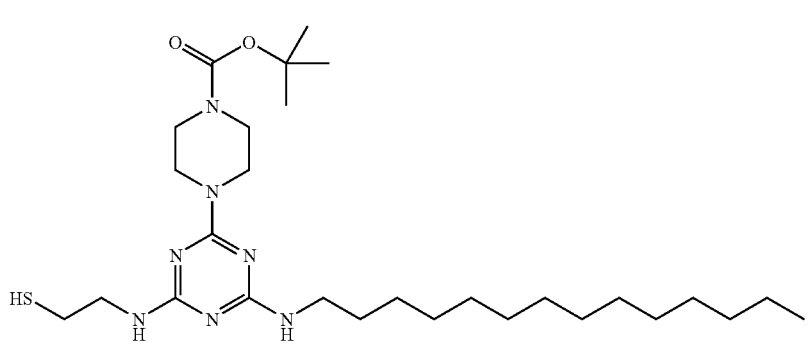

(11)

(c) Synthesis of the tert-butyl ester of {3-[4-(2-mercapto-ethylamine)-6-tetradecylamino-[1,3,5]triazin-2-yl-piperazinyl]}carbamic acid (11).

From a solution of (6) (204 mg) mixing for 24 hours, monitoring the progress in n-hexane/ethyl acetate 1:1 and chromatographing in n-hexane/ethyl acetate 1:1+ethyl acetate/methanol 7:3, is isolated (11) as a transparent oil, with a yield of 61%, $R_F$=0.35 (n-hexane/ethyl acetate 1:1) and the corresponding disulphide (12) as a yellow oil, with a yield of 8%, $R_F$=0.25 (n-hexane/ethyl acetate 1:1).

(13)

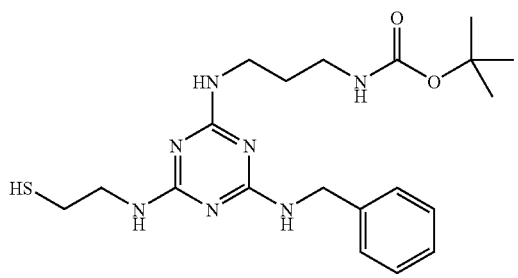

(d) Synthesis of the tert-butyl ester of {3-[4-(2-mercapto-ethylamine)-6-benzylamino-[1,3,5]triazin-2-ylamino]-propyl]carbamic acid (13). From a solution of (7) (157 mg) after 12 hours, monitoring the progress in n-hexane/ethyl acetate 4:6 and chromatographing in n-hexane/ethyl acetate 1:1, is isolated (13) as a transparent oil with a yield of 60%, $R_F$=0.35 (n-hexane/ethyl acetate 1:1).

(14)

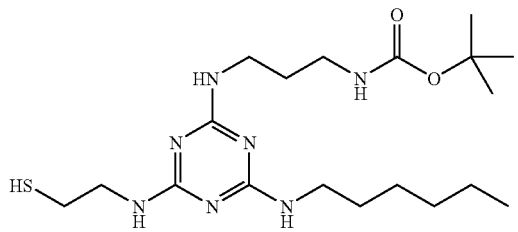

(e) Synthesis of the tert-butyl ester of {3-[4-(2-mercapto-ethylamine)-6-hexylamino-[1,3,5]triazin-2-ylamino]-propyl}carbamic acid (14). From a solution of (8) (155 mg) after 24 hours, monitoring the progress in n-hexane/ethyl acetate 4:6 and chromatographing in chloroform/methanol 97:3, is isolated (14) as a transparent oil with a yield of 79%, $R_F$=0.35 (n-hexane/ethyl acetate 4:6).

(f) Synthesis of the tert-butyl ester of [3-(4-dimethylamino-6-tetradecylamino-[1,3,5]triazin-2-ylamino)-propyl]carbamic acid (15). From a solution of (5) (1.0 mmol, 500 mg) and dimethylamine hydrochloride (50 mg) after 24 hours, monitoring the progress in n-hexane/ethyl acetate 3:7 and chromatographing in the same eluent mixture, is isolated pure (15) with a yield of 45%: $R_F$=0.35.

Isolation and Characterisation of the Final Compounds.

Method A. General Procedure. A 20% solution of trifluoroacetic acid in methylene chloride (10 ml) is added to a solution of tert-butylcarbamate 9-15 (0.16 mmol) in the same solvent (10 ml) and the reaction kept stirring using a magnetic stirrer for 1 hour at room temperature. The solvent is evaporated under reduced pressure to give the final compound as the trifluoroacetic salt.

(16)

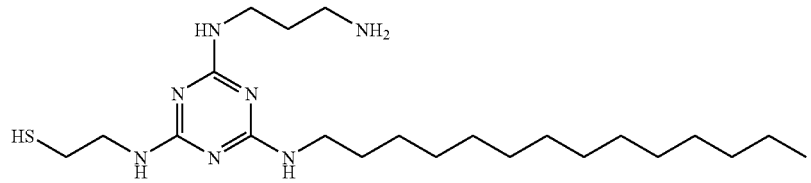

(a) Synthesis of the trifluoroacetic salt of 2-[4-(2-aminopropylamino)-6-tetradecylamino-[1,3,5]triazin-2-ylamino]-ethanethiol (16).

Starting from a solution of (9) (70 mg) compound (16) is obtained with a yield of 98%: $^1$H NMR (D$_2$O), δ: 3.65+3.55+3.43 (2H, m), 3.43 (2H, m), 3.31 (2H, m), 3.05 (2H, br t), 2.92+2.81+2.65 (2H, br s), 1.95 (2H, br t), 1.55 (2H, m), 1.75-1.20 (22H, br m), 0.85 (3H, br t, Me); $^1$H NMR (MeOD), δ: 3.73+3.62 (2H, br t, J=6.7 Hz), 3.52 (2H, br t, J=6.2 Hz), 3.39 (2H, m), 3.03 (2H, br t, J=7.4 Hz), 2.97+2.88+2.73 (2H, br t, J=6.9 Hz), 1.98 (2H, br t, J=7.4 and 6.7 Hz), 1.60 (2H, m), 1.45-1.20 (22H, br m), 0.88 (3H, br t, J=6.7 Hz, Me); $^1$H NMR (DMSO-d$_6$), δ: 8.4-8.0 (3H, br m, NH$_3$), 7.9-7.5 (3H, br m, 3×NH), 3.58+3.45 (2H, br t, J=6.7 Hz), 3.30 (4H, br m), 2.82 (4H, br m), 1.80 (2H, br m), 1.45 (2H, br m), 1.35-1.15 (22H, br m), 0.84 (3H, br t, Me); $^{19}$F NMR (DMSO-d$_6$), δ: −74.05 (s, 3F); $^{13}$C NMR (DMSO-d$_6$), δ: 169.9 (CO), 158.8, 114.0, 55.8, 36.9, 36.8, 36.3, 36.2, 31.2, 28.9, 28.6, 26.6, 26.1, 22.0, 13.8; IR (microscope): cm$^{-1}$ 3289 (s), 2926 (ss), 2855 (m), 1681 (ss), 1633 (ss), 1435 (m), 1338 (m), 1203 (m), 1139 (m), 1029 (m), 840 (m), 800 (m), 787 (m), 724 (m); Mass (EI, m/z, %): 438 (M$^+$+1, 100), 409 (94), 349 (90), 335 (25), 323 (20), 297 (10), 255 (12), 227 (14), 153 (26), 111 (23), 55 (98).

(15)

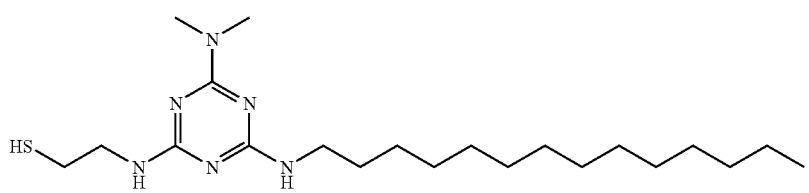

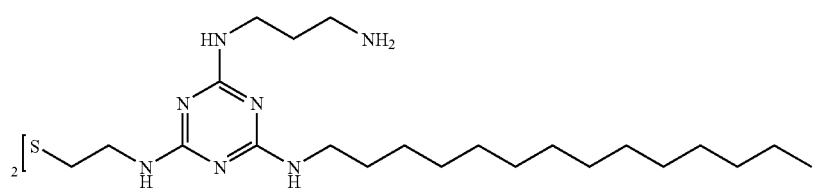

(17)

(b) Synthesis of the disulphide 17. Starting from a solution of (10) (140 mg) compound (17) is obtained with a yield of 98%: $R_f$=0.35 (ethyl acetate/methanol 1:1); $^1$H NMR (CDCl$_3$), δ: 6.0-4.0 (8H, broad signal, 8×NH), 3.75-3.55 (4H, m, CH$_2$), 3.50-3.30 (4H, m), 3.30-3.20 (4H, m), 3.05-2.80 (4H, m), 2.85-2.70 (4H, m), 1.75-1.60 (4H, m), 1.58-1.45 (4H, m), 1.38-1.17 (44H, br m), 0.88 (6H, t, J=6.0 Hz, 2×Me); Mass (EI, m/z, %): 877 (M$^+$+1, 12), 480 (8), 440 (80), 409 (100), 349 (68), 227 (50), 153 (38), 57 (18), 43 (15).

(e) Synthesis of the corresponding dimeric compound (19). Starting from a solution of (12) (150 mg) compound (19) is obtained with a yield of 90%: $^1$H NMR (CD$_3$OD), δ: 4.15 (8H, br m), 3.78 (4H, t, J=6.0 Hz), 3.40 (4H, dt, J=6.5 Hz), 3.30 (8H, br m), 2.92 (4H, br t, J=6.0 Hz), 1.61 (4H, br m), 1.40-1.20 (44H, br m), 0.90 (6H, br t, J=6.2 Hz, 2×Me); Mass (EI, m/z, %): 832 (240), 452 (30), 383 (100), 323 (15), 69 (18), 43 (45).

(18)

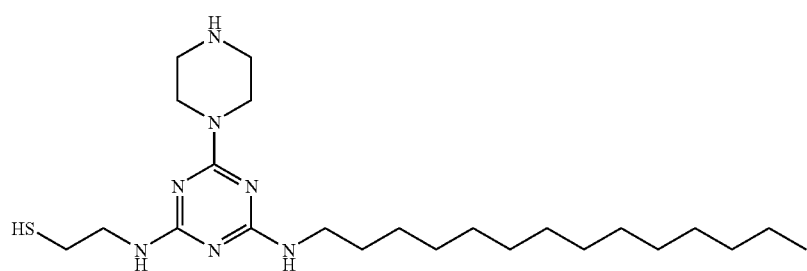

(c) Synthesis of the trifluoroacetic salt of 2-[4-(2-N-piperazinyl)-6-tetradecylamino-[1,3,5]triazin-2-ylamino]-ethanethiol (18). Starting from a solution of (11) (74 mg) compound (18) is obtained with a yield of 98%: $^1$H NMR (CD$_3$OD), δ: 4.80 (4H, br m), 3.61 (2H, dt, J=12.0 and 6.0 Hz), 3.40 (2H, dt, J=12.0 and 6.5 Hz), 3.25 (4H, br m), 2.66+2.84 (2H, br t, J=6.0 Hz), 1.61 (2H, br m), 1.40-1.20 (22H, br m), 0.84 (3H, br t, J=6.2 Hz, Me); $^{19}$F NMR (CD$_3$OD), δ: 74.23 (s, 3F, CF$_3$); $^{13}$C NMR (CD$_3$OD), δ: 164.4, 164.1, 163.8, 157.8 (CO), 118.3, 58.2, 46.0, 44.5, 42.2, 34.0, 32.2, 32.1, 32.0, 31.9, 31.8, 31.7, 31.6, 31.4, 30.8, 28.4, 25.0, 24.8, 14.8; Mass (EI, m/z, %): 568 (M$^+$+1, 20), 452 (34), 383 (90), 323 (15), 282 (5), 213 (2), 179 (4), 95 (20), 69 (83), 45 (100).

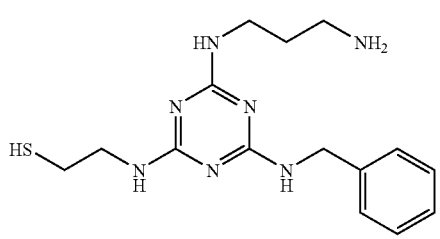

(20)

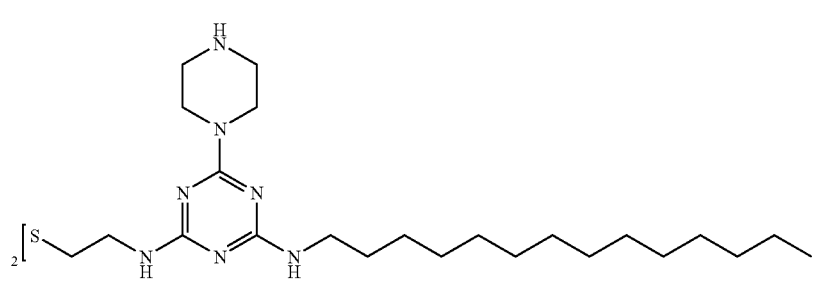

(19)

(e) Synthesis of the trifluoroacetic salt of 2-[4-(2-aminopropylamino)-6-benzylamino-[1,3,5]triazin-2-ylamino]-ethanethiol (20).

Starting from a solution of (13) (70 mg) compound (20) is obtained with a yield of 93%: $^1$H NMR (D$_2$O), δ: 7.4-7.1 (5H, brs, Ph), 4.61 (2H, m), 3.53 (2H, br m), 3.49 (2H, br m), 3.00 (2H, m, NH), 2.85 (2H, br m), 1.95 (2H, br m), 1.55 (2H, m); $^{13}$C NMR (CD$_3$OD), δ: 164.9, 162.0, 161.2, 157.0 (q, COCF$_3$), 130.0, 128.0, 117.1 (q, COCF$_3$), 57.0, 46.0, 45.0, $\overline{42.0}$, 38.2, 31.5; Mass (EI, m/z, %): $33\overline{4}$ (M$^+$+1, 40), 317 (14), 303 (20), 290 (10), 257 (12), 230 (8), 115 (16), 91 (43), 69 (98), 45 (100).

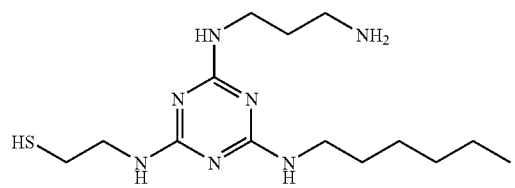

(21)

(f) Synthesis of the trifluoroacetic salt of 2-[4-(2-aminopropylamino)-6-hexylamino-[1,3,5]triazin-2-ylamino]-ethanethiol (21).

Starting from a solution of (14) (68 mg) compound (21) is obtained with a yield of 92%: $^1$H NMR (D$_2$O), δ: 3.78 (2H, m), 3.52 (2H, br m), 3.42 (2H, br m), 3.05 (2H, NH), 2.92 (2H, br m), 1.98 (2H, br m), 1.62 (2H, m), 1.32 (6H, m), 0.9 (3H, m, Me); $^{13}$C NMR (CD$_3$OD), δ: 165.0, 162.0, 161.3, 157.1 (q, COCF$_3$), 117.3 (q, COCF$_3$), 42.0, 41.3, 38.6, 38.1, 32.5, 30.0, $\overline{28.5}$, 28.2, 28.1, 23.6, $\overline{14.2}$; Mass (EI, m/z, %): 326 (M$^+$+1, 100), 284 (22), 251 (21), 237 (38), 224 (16), 95 (16), 69 (85), 45 (20).

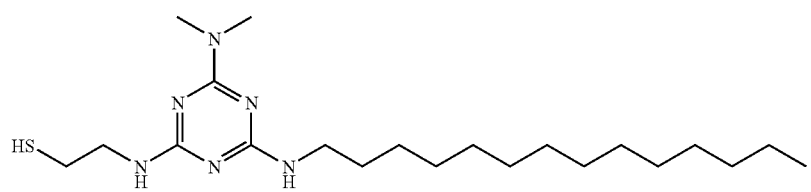

(22)

(g) Synthesis of the trifluoroacetic acid salt of N-(3-aminopropyl)-N'',N''-dimethyl-N'-tetradecyl-benzene-1,3,5-triamine (22). Starting from a solution of (15) (81 mg) compound (22) is obtained:

R$_F$=0.35 (n-hexane/ethyl acetate 1:9); $^1$H NMR (CDCl$_3$), δ:

5.10 (1H, br s, NH), 4.90 (1H, br s, NH), 6.25 (1H, broad signal, NH), 3.45 (2H, dt, J=6.0 and 5.8 Hz, CH$_2$), 3.33 (2H, m, J=6.6 and 6.0 Hz, CH$_2$), 3.08 (6H, br s, 2×Me), 2.78 2H, t, J=6.6 Hz, CH$_2$), 2, 18 (2H, broad signal, NH$_2$), 1.67 (2H, dt, J=6.6 and 6.4 Hz CH$_2$), 1.52 (2H, m, CH$_2$), 1.40-1.15 (22H, br m, 11×CH$_2$), 0.86 (3H, t, J=6.6 Hz, Me).

Cell Line Culture Transfection Tests.

Method

The plasmid vector PEGFP-N1 (BD Biosciences), containing the gene encoding green fluorescent protein (GFP) has been used in the transfection tests. Due to its properties, GFP is a useful tool for monitoring "passive" gene expression: indeed, fluorescent detection in this particular system is performed by means of cytofluorimetry or by microscopy.

Transfection tests have been performed on the cell line PC3 (human androgen-independent prostate carcinoma) with the plasmid PEGFP-N1 used in quantities equal to 2.5 and 5 μg. The general experimental outline envisaged 4 hours of transfection in reduced-serum culture medium, and in the absence of antibiotics. Upon completion of transfection, the culture medium has been replaced with normal growth medium and the evaluation of GFP expression has been performed 48 hours later by means of cytofluorimetry.

Results

In a first stage of the study, we wished to verify the capacity of compound 16 to induce the transfection of PC3 cells. Particularly, we tested 3 different charge ratios (CR 1.5, 3, 6) in the presence of 2.5 and 5 μg of pEGFP-N1 plasmid DNA. The evaluation of GFP expression, performed by flow cytometry 48 hours following transfection, has highlighted the presence of a significant percentage of GFP-positive cells (both living and total) with respect to the untreated cells (control) and the cells exposed to plasmid alone, which increased as a function of both the charge ratio and the amount of plasmid used, in the absence of any significant cellular toxicity (table 1). Subsequently, considering that the highest percentage of transfected cells, accompanied by low toxicity, was obtained with a charge ratio CR=6, we have verified the capacity of the derivatives of 16 (compounds 22, 17, 18, 20, 21, 19) to transfect PC3 cells. The results obtained have highlighted that compound 17 (the dimer of 16) was capable of inducing the transfection of PC3 cells. However, if compared with 16, compound 17 displayed greater toxicity, depending on the amount of plasmid used (table 2). Indeed, while at the lowest dose of PEGFP-N1, a higher percentage of transfected cells was obtained in comparison to that obtained with 16 (with equal quantities of plasmid), at the highest dose, the percentage of live transfected cells was reduced significantly, but in parallel, increased toxicity was observed (tables 1 and 2). However, it is interesting to point out that the total percentage of transfected cells increased as a function of the amount of plasmid DNA. On the contrary, compound 22, which under identical experimental conditions, induced the same percentage of toxicity observed following treatment with compound 17, was not capable of inducing significant transfection of the PC3 cells (table 2).

Transfection of PC3 cells, conducted in the presence of 5 μg of PEGFP-N1, has highlighted the fact that none of the following four compounds: 18, 19, 20 and 21 were capable of giving a significant percentage of living cells expressing the GFP protein. Furthermore, with the exception of compound 20 which did not show excessive levels of toxicity, the other 3 derivatives caused significantly greater cell mortality with respect to 16, 22 and 17 (table 2).

Once the transfection efficiency of compounds 16 and 17 had been established, we performed a comparative assessment of the two compounds with respect to the transfection capacities of Lipofectamine 2000 (Invitrogen) and DOTAP (Roche), commercially available cationic lipids, already widely used in analogous experiments. DOTAP and Lipofectamine 2000 were used in accordance with the instructions provided by the respective manufacturers.

The results obtained (table 3, graph 1) have shown that, for equal amounts of plasmid DNA used, compound 17 has shown itself to be capable of inducing a transfection efficiency comparable to that of Lipofectamine 2000, at both quantities of plasmid, but with a lesser degree of toxicity (table 3), while compound 16 was capable of inducing a transfection efficiency comparable to that of Lipofectamine 2000 only in the presence of higher quantities of plasmid DNA (graph 1; table 3). Hence we have assessed the transfection efficiencies of compounds 16 and 17 with respect to DOTAP. As reported in table 3 and in graph 1, the data obtained have highlighted that DOTAP, although less toxic, gave a lower percentage of transfection with respect to the two compounds, at both quantities of plasmid DNA tested. Finally, table 4 shows the preliminary data obtained from transfection of normal human thyrocytes (Line 636) and transformed human kidney cells (Line 293) in the presence of 16/pEGFP-N1 complexes (5 μg) at a charge ratio CR=6.

TABLE 1

Percentage of PC3 cells expressing GFP as a function of various 16/pEGFP-N1 charge ratios.

| | 2.5 μg pEGFP-N1 | | | 5 μg pEGFP-N1 | | |
|---|---|---|---|---|---|---|
| | Survival (*) | GFP+ living cells () | Total GFP+ cells () | Survival (*) | GFP+ living cells () | Total GFP+ cells () |
| Control | 100 | 0.86 | 3.90 | 100 | 1.22 | 1.81 |
| pEGFP-N1 | 79.2 | 1.00 | 3.73 | 85.0 | 0.12 | 0.64 |
| 16 CR = 1.5 | 71.4 | 1.18 | 4.75 | 100 | 1.54 | 1.85 |
| 16 CR = 3.0 | 79.8 | 4.05 | 7.81 | 96.0 | 10.6 | 12.45 |
| 16 CR = 6.0 | 86.3 | 32.40 | 46.13 | 64.4 | 64.6 | 70.70 |

(*) Data expressed as a percentage with respect to the control (untreated cells);
(**) Percentage of cells expressing GFP, evaluated by flow cytometry over a total of 10,000 events.

TABLE 2

Percentage of PC3 cells expressing GFP following transfection with derivatives of 16, at constant charge ratio (CR = 6).

| | 2.5 μg pEGFP-N1 | | | 5 μg pEGFP-N1 | | |
|---|---|---|---|---|---|---|
| | Survival (*) | GFP+ living cells () | Total GFP+ cells () | Survival (*) | GFP+ living cells () | Total GFP+ cells () |
| Control | 100 | 1.12 | 3.1 | 100 | 1.12 | 3.1 |
| pEGFP-N1 | 100 | 1.12 | 2.2 | 96.6 | 1.09 | 2.11 |
| 17 | 64.6 | 46.7 | 62.6 | 26.8 | 19.44 | 83.3 |
| 22 | 53.9 | 8.86 | 12.7 | 20.7 | 8.13 | 14.4 |
| 18 | — | — | — | 6.3 | 8.4 | 56.2 |
| 20 | — | — | — | 74.0 | 0.01 | 0.9 |
| 21 | — | — | — | 12.8 | 0.3 | 2.1 |
| 19 | — | — | — | 10.7 | 4.8 | 72.2 |

(*) Data expressed as a percentage with respect to the control (untreated cells);
(**) Percentage of cells expressing GFP, evaluated by flow cytometry over a total of 10,000 events.

TABLE 3

Comparison of PC3 cell transfection efficiency as a function of the various transfection agents.

| | 2.5 μg pEGFP-N1 | | | 5 μg pEGFP-N1 | | |
|---|---|---|---|---|---|---|
| | Survival (*) | GFP+ living cells () | Total GFP+ cells () | Survival (*) | GFP+ living cells () | Total GFP+ cells () |
| Control | 100 | 0.74 | 2.1 | 100 | 0.74 | 2.1 |
| pEGFP-N1 | 94.7 | 1.06 | 2.48 | 86.4 | 0.51 | 1.16 |
| Lipofect-2000 | 26.9 | 50.9 | 78.2 | 14.2 | 41.9 | 81.6 |
| DOTAP | 78.6 | 12.0 | 15.8 | 65.8 | 21.3 | 23.5 |
| 16 CR = 6.0 | 81.0 | 20.5 | 25.4 | 58.0 | 41.14 | 57 |
| 17 CR = 6.0 | 46.9 | 54.7 | 67.4 | 30.7 | 36 | 83 |

(*) Data expressed as mean percentage with respect to the control (untreated cells) obtained from a least 3 independent experiments;
(**) Percentage of cells expressing GFP, evaluated by flow cytometry over a total of 10,000 events, obtained from at least 3 independent experiments.

TABLE 4

Percentage of cells expressing GFP following transfection with 16 at charge ratio CR = 6.

| | 16/pEGFP-N1 (5 µg) | | |
|---|---|---|---|
| | Survival (*) | GFP+ living cells () | Total GFP+ cells () |
| Line 636 control | 100 | 2.2 | 3.1 |
| Line 636 | 75.3 | 34.3 | 53.8 |
| Line 293 control | 100 | 0.14 | 0.15 |
| Line 293 | 86.8 | 58.3 | 76.2 |

(*) Data expressed as a percentage with respect to the control (untreated cells);
(**) Percentage of cells expressing GFP, evaluated by flow cytometry over a total of 10,000 events.

The invention claimed is:

1. A compound of formula (I):

$$\begin{array}{c} R_1 \diagdown N \diagup R_2 \\ \mid \\ R_3 \diagdown N \diagup E \diagdown N \diagup R_6 \\ \mid \quad\quad\quad \mid \\ R_4 \quad\quad\quad R_5 \end{array} \quad (I)$$

wherein E is a 2,4,6-substituted 1,3,5-triazine;

R1 and R2, being identical or different, but never simultaneously equal to H, are selected from the group consisting of: H, —R7-NH$_2$, —CH$_2$—NH—NH$_2$, and a linear or branched alkyl with from 1 to 10 carbon atoms, or, R1 and R2, together with the nitrogen atom to which they are bound, form a 5 or 6 member heterocyclic ring or morpholine;

R7 is selected from the group consisting of: a linear or branched alkyl with from 2 to 10 carbon atoms; a linear or branched alkenyl, with from 3 to 10 carbon atoms and from 1 to 5 double bonds; an aryl; and a (C$_1$-C$_{20}$) alkyl-aryl-(C$_0$-C$_{20}$) alkyl;

R3 and R4, being identical or different, but never simultaneously equal to H, are selected from the group consisting of: H, —R8-SH, —R8-NH—NH$_2$, —R8-CO—R9, and —R8-NH$_2$, R8 is selected from the group consisting of: a linear or branched alkyl with from 2 to 10 carbon atoms; a linear or branched alkenyl, with from 3 to 10 carbon atoms and from 1 to 5 double bonds; an aryl; and a (C$_1$-C$_{20}$) alkyl-aryl-(C$_0$-C$_{20}$) alkyl;

R9 is selected from the group consisting of: H and a linear or branched alkyl with from 1 to 10 carbon atoms;

R5 and R6, being identical or different, but never simultaneously equal to H, are selected from the group consisting of: H, a linear or branched alkyl with from 6 to 20 carbon atoms, a linear or branched alkenyl with from 6 to 20 carbon atoms and with from 1 to 10 double bonds, and a (C$_1$-C$_{20}$) alkylaryl.

2. The compound according to claim 1, wherein R1 and R2 are selected from the group consisting of: H, —R7-NH$_2$, and linear alkyl with from 1 to 6 carbon atoms or, R$_1$ and R$_2$, together with the nitrogen atom to which they are bound, form a heterocycle selected from the group consisting of: 1,4-diazacyclohexane, 1,3-diazacyclohexane, 1,2-diazacyclohexane, piperidine, and pyrrolidine.

3. The compound according to claim 1, wherein R1 and R2 are selected from the group consisting of: H, methyl, ethyl, propyl, n-butyl, n-pentyl, and R7-NH$_2$ or, R1 and R2, together with the nitrogen to which they are bound, form 1,4-diazacyclohexane, 1,3-diazacyclohexane or 1,2-diazacyclohexane.

4. The compound according to claim 1, wherein R1 and R2 are H, —R7-NH$_2$, or methyl or, R1 and R2, together with the nitrogen to which they are bound, form 1,4-diazacyclohexane.

5. The compound according to claim 1, wherein R7 is a linear alkyl with from 2 to 6 carbon atoms, a benzyl, or a (C$_1$-C$_5$) alkyl-aryl-(C$_0$-C$_6$) alkyl.

6. The compound according to claim 1, wherein R7 is an ethyl, propyl, n-butyl, n-pentyl, benzyl, phenyl, or (C$_1$-C$_5$) alkyl-aryl-(C$_0$-C$_3$)alkyl.

7. The compound according to claim 1 wherein R7 is propyl, benzyl or phenyl.

8. The compound according to claim 1, wherein R3 and R4 are selected from the group consisting of: H, —R8-SH, and —R8-NH$_2$.

9. The compound according to claim 1 wherein R3 and R4 are H or —R8-SH.

10. The compound according to claim 1, wherein R8 is a linear alkyl with from 2 to 6 carbon atoms, a benzyl, or a (C$_1$-C$_5$) alkyl-aryl-(C$_0$-C$_6$) alkyl.

11. The compound according to claim 1, wherein R8 is ethyl, propyl, n-butyl, n-pentyl, benzyl, phenyl, or (C$_1$-C$_5$) alkyl-aryl-(C$_0$-C$_3$) alkyl.

12. The compound according to claim 1 wherein R8 is ethyl, benzyl or phenyl.

13. The compound according to claim 1, wherein R9 is selected from the group consisting of: a linear alkyl with from 1 to 4 carbon atoms and H.

14. The compound according to claim 1, wherein R9 is methyl, ethyl, or propyl.

15. The compound according to claim 1, wherein R5 and R6 are selected from the group consisting of: H, linear alkyl with from 6 to 14 carbon atoms, (C$_1$-C$_4$) alkyl-aryl, and benzyl.

16. The compound according to claim 1, wherein R5 and R6 are H, n-hexyl, n-tetradecanoyl, or phenyl.

17. The compound according to claim 1, of formula

18. The compound according to claim 1, of formula
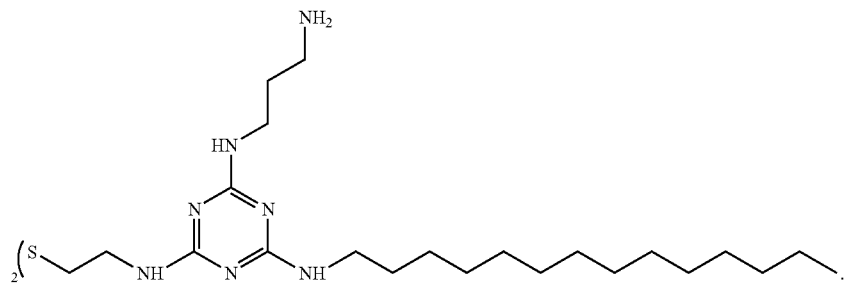
19. The compound according to claim 1, of formula
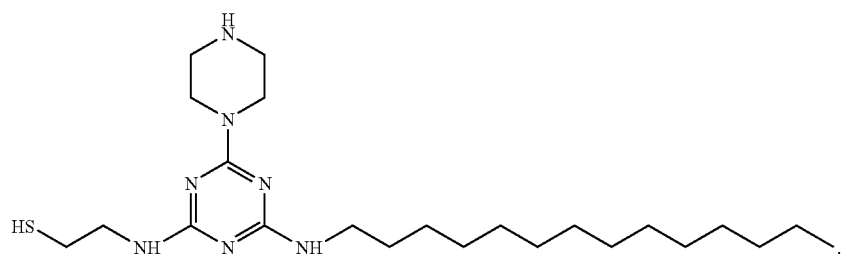
20. The compound according to claim 1, of formula
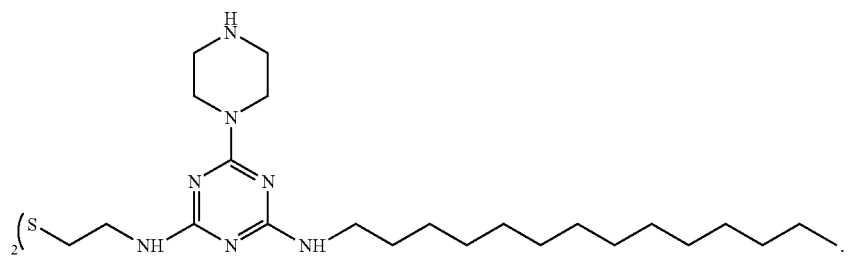
21. The compound according to claim 1, of formula
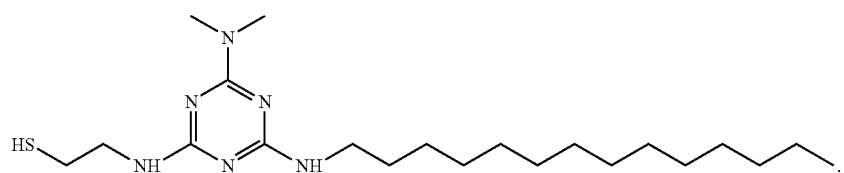
22. The compound according to claim 1, of formula
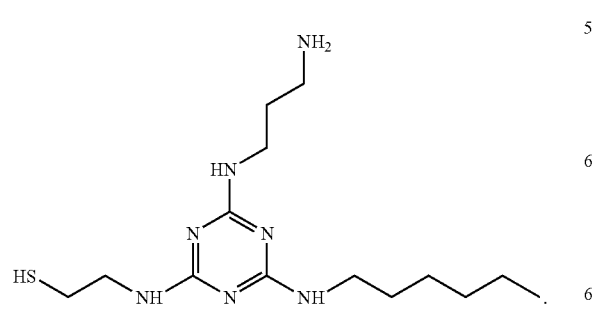
23. The compound according to claim 1, of formula:
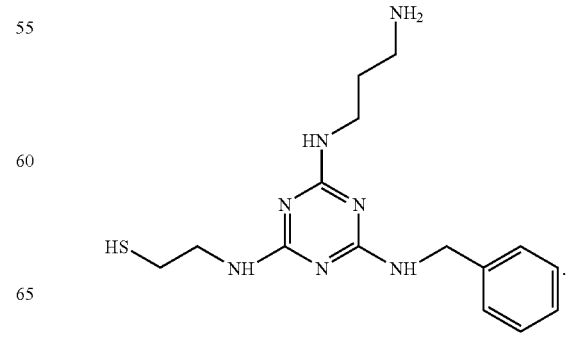

24. Nanoparticles condensed with one or more nucleic acids and one or more compounds of formula (Ix):

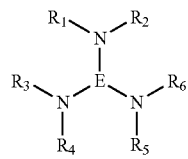
(Ix)

wherein E is a 2,4,6-substituted 1,3,5-triazine;
R1 and R2, being identical or different, but never simultaneously equal to H, are selected from the group consisting of: H, —R7-NH$_2$—CH$_2$—NH—NH$_2$, and a linear or branched alkyl with from 1 to 10 carbon atoms, or, R1 and R2, together with the nitrogen atom to which they are bound, form a 5 or 6 member heterocyclic ring or morpholine;
R7 is selected from the group consisting of: a linear or branched alkyl with from 2 to 10 carbon atoms; a linear or branched alkenyl, with from 3 to 10 carbon atoms and from 1 to 5 double bonds; an aryl; and a (C$_1$-C$_{20}$) alkyl-aryl-(C$_0$-C$_{20}$) alkyl;
R3 and R4, being identical or different, but never simultaneously equal to H, are selected from the group consisting of: H, —R8-SH, —R8-NH—NH$_2$, —R8CO—R9, and -R8-NH$_2$,
R8 is selected from the group consisting of: a linear or branched alkyl with from 2 to 10 carbon atoms; a linear or branched alkenyl, with from 3 to 10 carbon atoms and from 1 to 5 double bonds; an aryl; and a (C$_1$-C$_{20}$) alkyl-aryl-(C$_0$-C$_{20}$) alkyl;
R9 is selected from the group consisting of: H and a linear or branched alkyl with from 1 to 10 carbon atoms; and
R5 and R6, being identical or different, but never simultaneously equal to H, are selected from the group consisting of: H, a linear or branched alkyl with from 6 to 20 carbon atoms a linear or branched alkenyl with from 6 to 20 carbon atoms and with from 1 to 10 double bonds, an aryl and a (C$_1$-C$_{20}$) alkylaryl.

25. The nanoparticles according to claim 24 wherein said nucleic acids are DNA and/or RNA.

26. The nanoparticles according to claim 25 wherein the DNA is a plasmid.

27. The nanoparticles according to claim 26 wherein said plasmid encodes a therapeutically active molecule.

28. The nanoparticles according to claim 24 for use as a remedy.

29. A method for preparing a gene therapy remedy, comprising using the nanoparticles according to claim 24.

30. A method for the in vivo transfection of eukaryotic cells, comprising using the nanoparticles of claim 24.

31. A method for the in vitro transfection of eukaryotic cells, comprising using the nanoparticles of claim 24.

32. A method for preparing molecules of biological interest, comprising the method of in vitro transfection of eukaryotic cells according to claim 31.

33. A pharmaceutical composition comprising a therapeutically efficacious quantity of nanoparticles according to claim 24.

34. A method for the preparation of nanoparticles according to claim 24 comprising the following steps:
mixing the nucleic acids with the compounds of formula (I) in an appropriate buffer at physiological pH;
allowing the formation of the nucleic acids/compounds of formula (I) complex;
in a mildly oxidising environment, allowing the compounds of formula (I) to dimerise.

35. A kit for the preparation of nanoparticles according to claim 24, comprising genetic material, compounds of formula (I), buffers and other reagents and/or materials useful for preparing, purifying and applying the nanoparticles in vivo and in vitro.

36. The compound according to claim 1, wherein R9 is methyl or H.

37. The nanoparticles of claim 26, wherein said plasmid encodes a protein.

38. A pharmaceutically acceptable salt of a compound of formula (I):

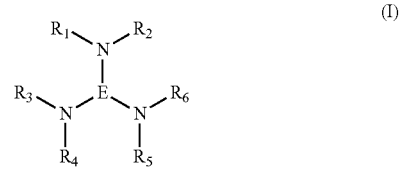
(I)

wherein E is triazine;
R1 and R2, being identical or different, but never simultaneously equal to H, are selected from the group consisting of: H, —R7-NH$_2$, —CH$_2$—NH—NH$_2$, and a linear or branched alkyl with from 1 to 10 carbon atoms, or, R1 and R2, together with the nitrogen atom to which they are bound, form a 5 or 6 member heterocyclic ring;
R7 is selected from the group consisting of: a linear or branched alkyl with from 2 to 10 carbon atoms; a linear or branched alkenyl, with from 3 to 10 carbon atoms and from 1 to 5 double bonds; an aryl; and a (C$_1$-C$_{20}$) alkyl-aryl-(C$_0$-C$_{20}$) alkyl; R3 and R4, being identical or different, but never simultaneously equal to H, are selected from the group consisting of: H, —R8-SH, —R8-NH—NH$_2$, —R8-CO—R9, and —R8-NH$_2$,
R8 is selected from the group consisting of: a linear or branched alkyl with from 2 to 10 carbon atoms; a linear or branched alkenyl, with from 3 to 10 carbon atoms and from 1 to 5 double bonds; an aryl; and a (C$_1$-C$_{20}$) alkyl-aryl-(C$_0$-C$_{20}$) alkyl;
R9 is selected from the group consisting of: H and a linear or branched alkyl with from 1 to 10 carbon atoms;
R5 and R6, being identical or different, but never simultaneously equal to H, are selected from the group consisting of: H, a linear or branched alkyl with from 6 to 20 carbon atoms, a linear or branched alkenyl with from 6 to 20 carbon atoms and with from 1 to 10 double bonds, and a (C$_1$-C$_{20}$) alkylaryl.

* * * * *